US012806272B2

(12) United States Patent
Lee et al.

(10) Patent No.: US 12,806,272 B2
(45) Date of Patent: Nov. 24, 2026

(54) TEMPERATURE-SENSITIVE HYDROGEL FOR CANCER TREATMENT CAPABLE OF PHOTOTHERMAL THERAPY AND PREPARATION METHOD THEREFOR

(71) Applicant: KOREA NATIONAL UNIVERSITY OF TRANSPORTATION INDUSTRY-ACADEMIC COOPERATION FOUNDATION, Chungju-si (KR)

(72) Inventors: Yong Kyu Lee, Chungju-si (KR); In Kyu Park, Nam-gu (KR); Adityanarayan Mohapatra, Hwasun-gun (KR); Jagannath Mondal, Chungju-si (KR); Jeong Man An, Chungju-si (KR)

(73) Assignee: KOREA NATIONAL UNIVERSITY OF TRANSPORTATION INDUSTRY ACADEMIC COOPERATION FOUNDATION, Chungju-si (KR)

( * ) Notice: Subject to any disclaimer, the term of this patent is extended or adjusted under 35 U.S.C. 154(b) by 239 days.

(21) Appl. No.: 18/843,167

(22) PCT Filed: Apr. 11, 2022

(86) PCT No.: PCT/KR2022/005225
§ 371 (c)(1),
(2) Date: Aug. 30, 2024

(87) PCT Pub. No.: WO2023/167364
PCT Pub. Date: Sep. 7, 2023

(65) Prior Publication Data

US 2025/0177532 A1 Jun. 5, 2025

(30) Foreign Application Priority Data

Mar. 2, 2022 (KR) ........................ 10-2022-0026836

(51) Int. Cl.

| | |
|---|---|
| ***A61K 41/00*** | (2020.01) |
| ***A61K 9/06*** | (2006.01) |
| ***A61K 31/198*** | (2006.01) |
| ***A61K 33/242*** | (2019.01) |
| ***A61K 45/06*** | (2006.01) |
| ***A61K 47/36*** | (2006.01) |
| ***A61P 35/00*** | (2006.01) |

(52) U.S. Cl.
CPC ............ *A61K 41/0052* (2013.01); *A61K 9/06* (2013.01); *A61K 31/198* (2013.01); *A61K 33/242* (2019.01); *A61K 45/06* (2013.01); *A61K 47/36* (2013.01); *A61P 35/00* (2018.01)

(58) Field of Classification Search
CPC .............. A61K 41/0052; A61K 33/242; A61K 31/198; A61K 9/06; A61K 47/36; A61P 35/00
See application file for complete search history.

(56) References Cited

U.S. PATENT DOCUMENTS

2018/0133319 A1 5/2018 Vo-Dinh et al.

FOREIGN PATENT DOCUMENTS

KR 10-1756962 B1 7/2017
KR 10-2070580 B1 3/2020

OTHER PUBLICATIONS

Korean Patent Office, Request for the Submission of an Opinion, Application No. 10-2022-026836, dated Mar. 18, 2024, in 6 pages.
Chen, et al., "Multifunctional Gold Nanostar Conjugates for Tumor Imaging and Combined Photothermal and Chemo-therapy", Theranostics 2013, vol. 3, Issue 9, dated Aug. 3, 2013, in 17 pages.
Peng, et al., "Photosensitizer Micelles Together with IDO Inhibitor Enhance Cancer Photothermal Therapy and Immunotherapy", Advanced Science, 2018, in 15 pages.
Ratanatawanate, et al., "S-Nitrosocysteine-Decorated PbS QDs/TiO2 Nanotubes for Enhanced Production of Singlet Oxygen", Journal of the American Chemical Society, Feb. 22, 2011, in 6 pages.
Patent Cooperation Treaty, International Search Report, Application No. PCT/KR2022/005225, dated Nov. 23, 2022, in 4 pages.

*Primary Examiner* — Alicia L Otton
(74) *Attorney, Agent, or Firm* — PROCOPIO, CORY, HARGREAVES & SAVITCH LLP

(57) ABSTRACT

The present invention relates to: a temperature-sensitive hydrogel for cancer treatment; a photothermal composition comprising the hydrogel as an active ingredient; and a preparation method for the temperature-sensitive hydrogel for cancer treatment. The temperature-sensitive hydrogel of the present invention includes gold nanostars as active ingredients, and thus can generate heat by light irradiation, thereby exhibiting a photothermal therapy effect. In addition, the hydrogel temperature increases so that the release of nitric oxide (NO) from S-nitrosocysteine can be induced. In addition, the temperature-sensitive hydrogel of the present invention includes S-nitrosocysteine as an active ingredient so that, upon a temperature rise due to a photothermal reaction, the penetration of drugs into a tumor site can be improved by the release of NO, and at the same time, apoptosis of cancer cells can be directly caused; and includes an immunotherapy agent as an active ingredient so that tumor size can be effectively suppressed even with the passage of time. Therefore, as a material that enables complex treatment combined with photothermal therapy and immunotherapy, the temperature-sensitive hydrogel of the present invention having the aforementioned effect can be usefully utilized in the field of medicine for cancer treatment.

12 Claims, 21 Drawing Sheets

| | | | Size (d.nm): | % Intensity: | St Dev (d.nm): |
|---|---|---|---|---|---|
| Z-Average (d.nm): | 89.29 | Peak 1: | 110.0 | 100.0 | 37.15 |
| PdI: | 0.199 | Peak 2: | 0.000 | 0.0 | 0.000 |
| Intercept: | 0.907 | Peak 3: | 0.000 | 0.0 | 0.000 |
| Result quality : | Good | | | | |

TEMPERATURE-SENSITIVE HYDROGEL FOR CANCER TREATMENT CAPABLE OF PHOTOTHERMAL THERAPY AND PREPARATION METHOD THEREFOR

CROSS-REFERENCE TO RELATED APPLICATIONS

This application is US National Stage of International Patent Application PCT/KR2022/005225, filed Apr. 11, 2022, which claims benefit of priority from Korean Patent Application 10-2022-0026836, filed Mar. 2, 2022, the contents of both of which are incorporated herein by reference.

TECHNICAL FIELD

The present invention relates to a temperature-sensitive hydrogel for treating cancer, a photothermal composition containing the hydrogel as an active ingredient, and a method of preparing a temperature-sensitive hydrogel for treating cancer.

BACKGROUND ART

Cancer, which is caused by various types of stress and pollution, is a disease that accounts for the largest proportion of deaths among modern people. Cancer refers to a malignant tumor that is caused by gene mutation in normal cells, does not follow the differentiation and growth patterns of normal cells and does not undergo apoptosis. Methods of treating cancer include surgical treatment, chemical treatment, radiation therapy, immunotherapy, and photothermal treatment.

Photothermal therapy refers to a therapy that accumulates a heat-generating substance absorbing near-infrared light at locations requiring hyperthermia and irradiates the heat-generating substance with near-infrared light. Near-infrared light is poorly absorbed in body tissues, thus increasing the depth of the body at which local treatment is possible and minimizing damage to tissues excluding the location where the material has accumulated.

Photothermal therapy has been widely researched with the goal of non-invasive tumor ablation for decades and recent research has showed that photothermal therapy may exhibit synergetic effects in combination with other therapy such as gas therapy, chemotherapy, and immunotherapy. Massive nanomaterials such as black phosphorus, carbon-based nanomaterials, metal oxides or transition metal oxides have been studied as exothermic agents. These nanomaterials are unstable when they are subjected to multiple near-infrared laser irradiation and thus have limited applications to tumor treatment. However, plasmonic gold nanostars (GNS) have proven to have potential due to higher photothermal conversion efficiency thereof than other types of gold nanoparticles. Recent research showed that photothermal therapy alone causes tumor recurrence after a predetermined period of time. Therefore, there is an urgent need for combination treatment of photothermal therapy with chemotherapy, immunotherapy or the like for complete tumor treatment.

Meanwhile, nitric oxide (NO) is a molecular transmitter that functions to relax vascular smooth muscles, increase blood flow, and improve vascular permeability. In addition, a high concentration of NO suppresses tumors and directly and effectively kills cells through apoptosis or necrosis. In addition, NO has been reported to change the multidrug resistance (MDR) of cancer cells by reducing P-glycoprotein (P-gp) expression levels to inhibit tumor growth and metastasis.

Under this background, the present inventors tried to develop a material that provides a combination treatment of photothermal therapy and immunotherapy in order to completely treat tumors while preventing tumor recurrence. As a result, the present inventors prepared a temperature-sensitive hydrogel containing gold nanostars, S-nitrosocysteine, and an immunotherapeutic agent. The present inventors found that the hydrogel exhibits a photothermal effect when irradiated with a near-infrared laser and penetrates the drug into deeper tumor sites when nitric oxide (NO) is released as the temperature rises, and directly causes apoptosis due to a high concentration of NO. In addition, the present inventors found that the hydrogel of the present invention contains an immunotherapeutic agent as an active ingredient, thereby effectively reducing tumor size even over time after photothermal therapy compared to the hydrogel not containing an immunotherapeutic agent. The present invention has been completed based on this finding.

DISCLOSURE

Technical Problem

It is one object of the present invention to provide a temperature-sensitive hydrogel for treating cancer that enables both photothermal therapy and immunotherapy.

It is another object of the present invention to provide a photothermal composition containing the hydrogel as an active ingredient.

It is yet another object of the present invention to provide a method of preparing the temperature-sensitive hydrogel for treating cancer.

Technical Solution

In accordance with one aspect of the present invention, the above and other objects can be accomplished by the provision of a temperature-sensitive hydrogel for treating cancer containing gold nanostars, S-nitrosocysteine, and an immunotherapeutic agent as active ingredients.

In one embodiment of the present invention, the gold nanostars may generate heat when irradiated with light.

In one embodiment of the present invention, the immunotherapeutic agent may be a stimulator of interferon genes, an indoleamine 2,3-dioxygenase (IDO) inhibitor, or a combination thereof.

In one embodiment of the present invention, the hydrogel may further contain a gelling polymer.

In one embodiment of the present invention, the gelling polymer may include at least one selected from the group consisting of hyaluronic acid, Pluronic, purified agar, agarose, gellan gum, alginic acid, carrageenan, *cassia* gum, xanthan gum, galactomannan, glucomannan, pectin, cellulose, guar gum and locust bean gum.

In one embodiment of the present invention, the hydrogel may generate heat and release nitric oxide (NO) when irradiated with near-infrared light.

In accordance with another aspect of the present invention, provided is a photothermal composition for treating cancer containing the temperature-sensitive hydrogel as an active ingredient.

In one embodiment of the present invention, the cancer may be selected from the group consisting of brain tumor, benign astrocytoma, malignant astrocytoma, pituitary adenoma, meningioma, cerebral lymphoma, oligodendroglioma, intracranial tumor, ependymoma, brainstem tumor, head and neck tumor, laryngeal cancer, oropharyngeal cancer, nasal cancer, nasopharyngeal cancer, salivary gland cancer, hypopharyngeal cancer, thyroid cancer, oral cancer, thoracic tumor, small cell lung cancer, non-small cell lung cancer, thymic cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colon cancer, anal cancer, bladder cancer, kidney cancer, male genital tract tumor, penile cancer, prostate cancer, female genital tract tumor, cervical cancer, endometrial cancer, ovarian cancer, uterine sarcoma, vaginal cancer, female external genital cancer, female urethral cancer, and skin cancer.

In one embodiment of the present invention, the composition may be a composition for subcutaneous injection, intramuscular injection, intraperitoneal injection, transdermal injection, or intralesional injection.

In accordance with another aspect of the present invention, provided is a method of preparing a photothermal composition for treating cancer including: a) synthesizing S-nitrosocysteine; b) synthesizing gold nanostars; c) mixing a gelling polymer, S-nitrosocysteine, gold nanostars, and water; and d) adding an immunotherapeutic agent to the mixture obtained in step c), followed by stirring.

In one embodiment of the present invention, the gelling polymer may include at least one selected from the group consisting of hyaluronic acid, Pluronic, purified agar, agarose, gellan gum, alginic acid, carrageenan, cassia gum, xanthan gum, galactomannan, glucomannan, pectin, cellulose, guar gum and locust bean gum.

In one embodiment of the present invention, the immunotherapeutic agent may be a stimulator of interferon genes, an indoleamine 2,3-dioxygenase (IDO) inhibitor, or a combination thereof.

Advantageous Effects

The temperature-sensitive hydrogel of the present invention contains gold nanostars as an active ingredient and thus generates heat upon irradiation with light, to provide photothermal therapy effects. In addition, the temperature-sensitive hydrogel can increase the temperature of the hydrogel, thus inducing the release of nitric oxide (NO) from S-nitrosocysteine. In addition, the temperature-sensitive hydrogel according to the present invention contains S-nitrosocysteine as an active ingredient, thus improving drug penetration into the tumor site due to the release of nitric oxide (NO) when the temperature rises due to photothermal reaction and directly causing cancer cell death. Also, the temperature-sensitive hydrogel contains an immunotherapeutic agent as an active ingredient, thus effectively suppressing tumor size over time. Therefore, the temperature-sensitive hydrogel according to the present invention, which has the effects described above, is a material that enables combination treatment of photothermal therapy and immunotherapy and this is useful for the pharmaceutical field for cancer treatment.

9I shows the standard curve for quantitative analysis using the absorbance of nitric oxide (NO).

Figure 10A:
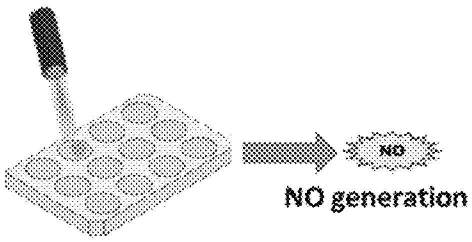
Figure 10B:
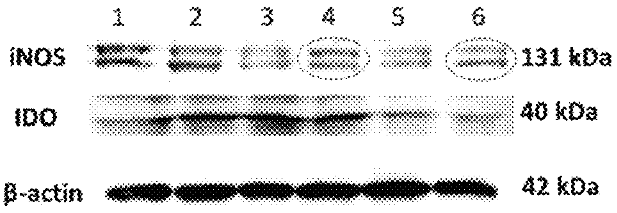

FIG. 10A is a schematic diagram illustrating release of nitric oxide (NO) under near-infrared laser irradiation (808 nm, 1.5 W/cm$^2$, 5 min). FIG. 10B shows the protein expression levels of iNOS and IDO in 4T1 cells treated by PBS (lane 1), IFN-γ (lane 2), GNS+CysNO (lane 3), CysNO+laser (lane 4), GNS+laser (lane 5) and GNS+CysNO+Laser (lane 6).

Figure 11:
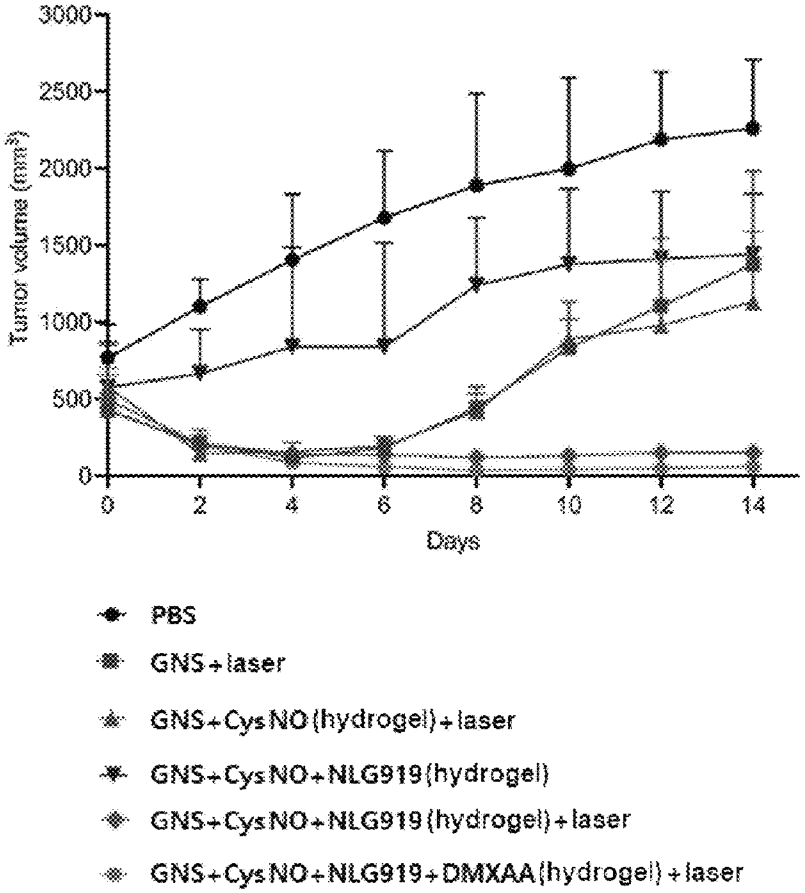

FIG. 11 is a graph showing tumor volume of the breast cancer animal model (mice with 4T1 tumors) during the photothermal therapy (N=5).

Figure 12:
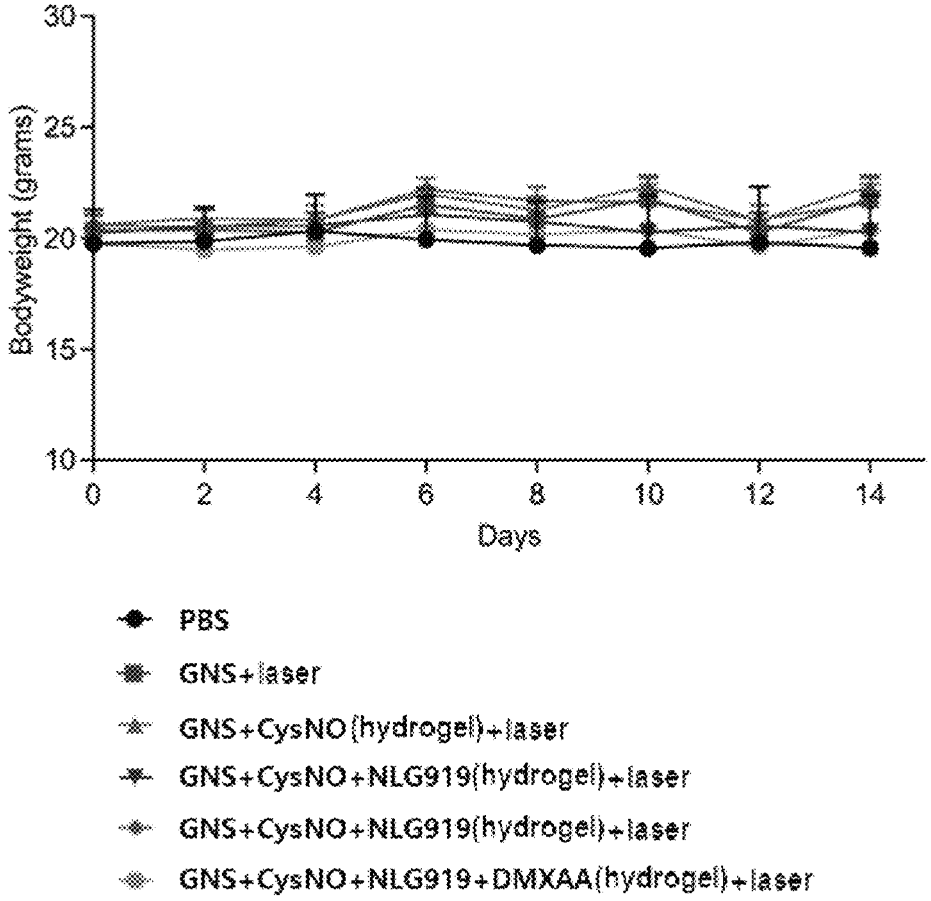

FIG. 12 is a graph showing changes in body weight of the breast cancer animal model (mice with 4T1 tumors) during the photothermal therapy (N=5).

Figure 13:
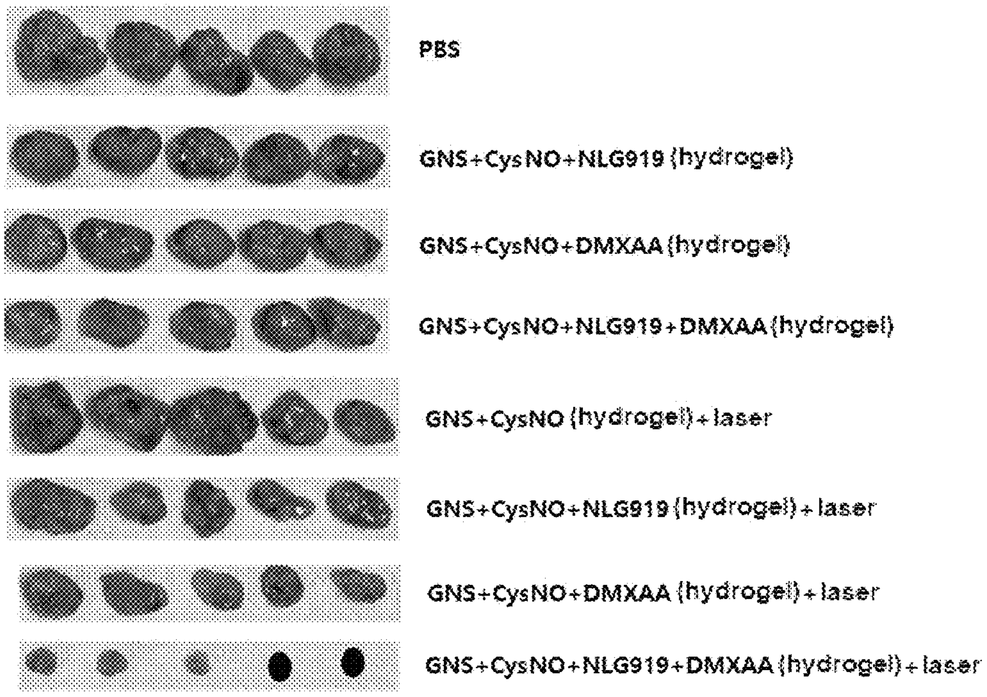

FIG. 13 is a photographic image of a tumor isolated from a breast cancer animal model (mice bearing 4T1 tumors) that received photothermal therapy (N=5).

BEST MODE

The present invention relates to a temperature-sensitive hydrogel for treating cancer containing gold nanostars, S-nitrosocysteine, and an immunotherapeutic agent as active ingredients.

As used herein, the term "gold nanostars" refers to star-shaped gold nanoparticles.

The gold nanostars of the present invention can generate heat through light irradiation, thus causing a photothermal therapy effect. In addition, the gold nanostars increases the temperature of the hydrogel, thus inducing the release of nitric oxide (NO) from S-nitrosocysteine.

S-nitrosocysteine of the present invention is a compound having the structure represented by the following formula, in which the hydrogen atom of the thiol group (—SH) of cysteine is replaced with a nitroso group (—NO).

[Formula]

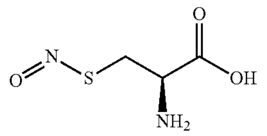

S-nitrosocysteine of the present invention improves drug penetration into the tumor site due to the release of nitric oxide (NO) when the temperature of the hydrogel increases due to photothermal reaction, and at the same time directly causes cancer cell death.

As used herein, the term "immunotherapeutic agent" refers to an agent that activates immune function to treat cancer.

Generally, when a tumor is removed by photothermal therapy, the tumor grows again after a predetermined period of time. The immunotherapeutic agent of the present invention plays an important role in completely eliminating tumors by effectively suppressing tumor size even over time after photothermal therapy.

In one embodiment of the present invention, the immunotherapeutic agent may be a stimulator of interferon genes, an indoleamine 2,3-dioxygenase (IDO) inhibitor, or a combination thereof.

As used herein, the term "stimulator of interferon genes (STING)" refers to an adapter protein acting as an essential ingredient of the innate immune system that responds to microbial DNA. The stimulator of interferon genes (STING) acts to induce DC maturation and T cell proliferation by activating interferon.

In one embodiment of the present invention, examples of the stimulator of interferon genes (STING) include ADU-S100, BMS-986301, E7766, GSK-3745417, MK-1454, MK-2118, SB11285, amino-benzimidazole (diABZI), DMXAA (5,6-dimethylxanthenone-4-acetic acid) and the like. The stimulator of interferon genes (STING) is preferably DMXAA (5,6-dimethylxanthenone-4-acetic acid).

As used herein, the term "IDO (indoleamine 2,3-dioxygenase)" is an enzyme that decomposes tryptophan to produce kynurenine. In this process, the IDO acts to inhibit the activity of immune cells, including T cells, through various mechanisms.

As used herein, the term "IDO (indoleamine 2,3-dioxygenase) inhibitor" is a substance that inhibits the indoleamine 2,3-dioxygenase enzyme and acts to inhibit proliferation of MDSC (myeloid-derived suppressor cells) and $T_{reg}$ cells that inhibit cell death.

In one embodiment of the present invention, examples of the IDO inhibitor may include Epacadostat, BMS-986205, PF-06840003, LY3381916, Indoximod, NLG802, NLG919, and the like. The IDO inhibitor is preferably NLG919.

The temperature-sensitive hydrogel for treating cancer according to the present invention may further contain a gelling polymer as an active ingredient.

In one embodiment of the present invention, the gelling polymer may include at least one selected from the group consisting of hyaluronic acid, Pluronic, purified agar, agarose, gellan gum, alginic acid, carrageenan, *cassia* gum, xanthan gum, galactomannan, glucomannan, pectin, cellulose, guar gum and locust bean gum. The gelling polymer is preferably a combination of hyaluronic acid and Pluronic.

In one embodiment of the present invention, the temperature-sensitive hydrogel may generate heat and release nitric oxide (NO) when irradiated with near-infrared light.

The present invention provides a photothermal composition for treating cancer containing the temperature-sensitive hydrogel as an active ingredient.

In one embodiment of the present invention, the cancer may be selected from the group consisting of brain tumor, benign astrocytoma, malignant astrocytoma, pituitary adenoma, meningioma, cerebral lymphoma, oligodendroglioma, intracranial tumor, ependymoma, brainstem tumor, head and neck tumor, laryngeal cancer, oropharyngeal cancer, nasal cancer, nasopharyngeal cancer, salivary gland cancer, hypopharyngeal cancer, thyroid cancer, oral cancer, thoracic tumor, small cell lung cancer, non-small cell lung cancer, thymic cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colon cancer, anal cancer, bladder cancer, kidney cancer, male genital tract tumor, penile cancer, prostate cancer, female genital tract tumor, cervical cancer, endometrial cancer, ovarian cancer, uterine sarcoma, vaginal cancer, female external genital cancer, female urethral cancer, and skin cancer. The cancer is preferably breast cancer.

Breast cancer is prevalent in women worldwide and leading cause of death by cancer among women every year. It is expected that around 1.7 million cases diagnosed for breast cancer every year and it alone account for 30% of all female cancers. A successful treatment of breast cancer needs to target more than one signaling pathway due to the complex nature of tumor environment in breast tissue as well as elimination of highly overexpressed of P-glycoprotein or breast cancer resistant protein. Therefore, a certain strategy is urgently required to enhance sufficient drug accumulation in tumors to have better therapeutic efficacy and inhibit metastasis.

In the following examples according to the present invention, a temperature-sensitive hydrogel (containing gold nanostars, S-nitrosocysteine, and an immunotherapeutic agent) is subcutaneously injected into a breast cancer animal model and irradiated with near-infrared light for 10 minutes, and then the size of the tumor was measured for 14 days. The result showed that the size of the tumor was effectively reduced and the growth of the tumor was delayed even over time. In particular, in the temperature-sensitive hydrogel that did not contain an immunotherapy agent, the tumor was found to grow again over time after photothermal therapy, whereas in the temperature-sensitive hydrogel invention containing an immunotherapeutic agent according to the present, the tumor did not grow over time and became smaller.

Therefore, the present invention proved based on experiments that the temperature-sensitive hydrogel can effectively treat tumors through a combination of phototherapy and immunotherapy strategies.

The photothermal composition for treating cancer according to the present invention contains, as an active ingredient, the temperature-sensitive hydrogel according to the present invention exhibiting the effects described above, and is used selectively for photothermal therapy of local areas.

The photothermal composition for treating cancer according to the present invention may be administered parenterally to the biological tissues of mammals, including humans, through various routes. For example, the photothermal composition may be administered using any one method selected from intravenous injection, subcutaneous injection, intramuscular injection, intraperitoneal injection, transdermal administration, and intralesional injection.

The appropriate dosage of the photothermal composition for treating cancer according to the present invention depends on factors such as formulation method, administration method, the age, weight, gender, and pathological condition of the patient, food, administration time, administration route, excretion rate, and reaction sensitivity. A general skilled physician can easily determine and prescribe an effective dosage for the desired treatment or prevention. For example, the daily dosage may be 0.0001 to 1,000 mg/kg.

After injecting the photothermal composition for treating cancer according to the present invention into a human body and then irradiating the photothermal composition with light to generate heat, the photothermal composition may be used to treat various diseases related to cancer, such as stomach cancer, lung cancer, breast cancer, ovarian cancer, liver cancer, bronchial cancer, nasopharyngeal cancer, laryngeal cancer, pancreatic cancer, bladder cancer, colon cancer, or cervical cancer.

To perform photothermal therapy using the photothermal composition for treating cancer according to the present invention, the photothermal composition of the present invention is administered to the body of a human or a mammal other than the human, and then light is irradiated from outside the body. The light may be near-infrared light. For example, the body of the human or a mammal other than the human is irradiated using a near-infrared laser with a wavelength of 700 to 1, 000 nm.

Light irradiation is preferably performed at an intensity of 1 $mW/cm^2$ to 100 $W/cm^2$ once or repeatedly several times for 1 to 30 minutes.

The photothermal composition for treating cancer according to the present invention continuously exhibits photothermal effects above 50 °C for 6 days or longer when irradiated with near-infrared rays after injection, allowing relatively long-term photothermal therapy with a single administration. In particular, heat generation upon light irradiation increases the temperature of the hydrogel, leading to the release of nitric oxide (NO) from S-nitrosocysteine.

The present invention provides a method of preparing a photothermal hydrogel for treating cancer including: 1) mixing a gelling polymer, S-nitrosocysteine, gold nanostars, and water; and 2) adding an immunotherapeutic agent to the mixture obtained in step 1), followed by stirring.

In step 1), the S-nitrosocysteine and gold nanostars may be commercially available or may be synthesized directly.

The present invention provides a method of preparing a photothermal hydrogel for treating cancer including: a) synthesizing S-nitrosocysteine; b) synthesizing gold nanostars; c) mixing a gelling polymer, S-nitrosocysteine, gold nanostars, and water; and d) adding an immunotherapeutic agent to the mixture obtained in step c), followed by stirring.

In step a), S-nitrosocysteine is synthesized. More specifically, S-nitrosocysteine may be synthesized by the steps of: dissolving cysteine in hydrochloric acid (1M) and reacting the resulting solution with sodium nitrite in the absence of light; adding acetone to the resulting mixture and centrifuging the result to obtain a precipitate; and washing and drying the precipitate.

In step b), gold nanostars are synthesized. More specifically, gold nanostars are synthetized synthesized by steps of: adding a 1% citrate solution to a HAuCl4 solution (1 mM), heating the resulting solution, and cooling the resulting solution to room temperature when the solution turns dark red; stirring the cooled solution in the HAuCl4 solution (0.5 mM); reacting the stirred solution with an AgNO3 solution (3 mM) and ascorbic acid (100 mM); and centrifuging the reaction solution when the reaction solution turns dark blue.

In step c) of the present invention, the gelling polymer, S-nitrosocysteine, gold nanostars, and water are mixed with each other. Specifically, the gelling polymer, S-nitrosocysteine and gold nanostars are mixed at a weight ratio of 20 to 25:0.5 to 1:0.1 to 0.2 with water.

In step d) of the present invention, an immunotherapeutic agent is added to the mixture obtained in step c), followed by stirring. Specifically, the immunotherapeutic agent is added at a concentration of 0.1 to 5 mg/mL to the mixture obtained in step c), followed by stirring at 4 °C for 10 to 20 hours.

In one embodiment of the present invention, the gelling polymer may include at least one selected from the group consisting of hyaluronic acid, Pluronic, purified agar, agarose, gellan gum, alginic acid, carrageenan, *cassia* gum, xanthan gum, galactomannan, glucomannan, pectin, cellulose, guar gum and locust bean gum. Preferably, the gelling polymer is a combination of hyaluronic acid and Pluronic.

In another embodiment of the present invention, the immunotherapeutic agent may be a stimulator of interferon genes, an indoleamine 2,3-dioxygenase (IDO) inhibitor, or a combination thereof.

Hereinafter, the present invention will be described in detail with reference to Examples. The following Examples are provided only for illustration of the present invention and should not be construed as limiting the scope of the present invention.

MODE FOR INVENTION

Example

1. Materials and Methods

Materials

BSA, Traut's reagent, $HAuCl_4$, $AgNO_3$, fluorescein diacetate, propidium iodide, FITC, Pluronic F127, and hyaluronic acid were purchased from Sigma Aldrich; Amicon filter tube was purchased from Merck Millipore; NLG919 was purchased from BOC science; DMXAA (5,6-dimethylxanthenone-4-acetic acid) was purchased from Qingdao Kaimosi Biochemical Technology Co., Ltd.; 4T1 cells were purchased from Korean cell bank; primary antibodies (anti-iNOS, anti-IDO) were purchased from Cell Signaling; and BALB/C mice were purchased from Orient.

Synthesis of BSA-SNO, GSH-SNO and CysNO

In order to bind nitric oxide to bovine serum albumin (BSA), a BSA solution was first prepared using 0.1 M sodium phosphate buffer containing 2 mM EDTA (10 mg BSA mL-1). Traut's reagent (2-iminothiolane) was prepared at a concentration of 2 mg mL-1, mixed with the BSA solution at a ratio of 1:50 (BSA: 2-iminothiolane) (v/v), and reacted for 3 hours. After the reaction, BSA (BSA-SH) into which —SH group was introduced was purified using an Amicon filter tube. 0.1 g of the BSA-SH was dissolved in 1 ml of 0.5M HCl, 8 mg of $NaNO_2$ was added to the resulting solution and reacted for 30 min to synthesize the final product, called "BSA-SNO" into which —SNO group was introduced, and the final product was dialyzed for 48 hours (MWCO: 12-14 kDa). The purified BSA-SNO was stored in a freezer (−18 °C.).

In order to bind nitric oxide to glutathione (GSH) and cysteine (Cys), 270 mg of each of GSH and Cys was dissolved in 1.5 ml of a cold 1M HCl solution, 58 mg of $NaNO_2$ was added to the resulting solution, wrapped in foil to protect from light and reacted for 40 min. Then, 30 mL of cold acetone was added to the solution and centrifuged (2,500 RPM, 10 min) to obtain a red precipitate. The precipitate was washed twice with acetone and three times with ether, then dried in a vacuum oven at 25 °C for 2 hours to synthesize the final products, called "GSH-SNO" and "CysNO" into which —SNO groups were introduced. The Griess assay was performed to confirm the formation of —SNO in as synthesized molecules.

Synthesis of Gold Nanostars (GNS)

15 mL of a 1% citrate solution was added to 100 mL of a 1 mM $HAuCl_4$ solution and boiled. After the color turned into dark red the reaction was kept in room temperature for cooling. 500 μL of the cooled solution was added to 50 ml of a 0.5 mM $HAuCl_4$ solution, followed by stirring at 1, 000 rpm. Then, 500 μL of an $AgNO_3$ solution (3 mM) and 1 mL of ascorbic acid (100 mM) were added to the solution. When the color of the reaction solution changed to dark blue, GNS was purified by centrifugation (10,000 rpm, 15 min).

Preparation of Temperature-Sensitive Hydrogel Containing GNS, CysNO, and Immunotherapeutic Agent Pluronic F127 (20% w/v), BSA (1% w/v), hyaluronic acid (1% w/v), GNS (0.1% w/v), and CysNO (0.5% w/v) were added to 3 ml of distilled water and mixed at 4 °C for 24 hours. Then, DMXAA (0.4% w/v) and/or NLG919 (0.2% w/v) were added to the resulting mixture, followed by stirring at 4 °C for 12 hours. The completed temperature-sensitive hydrogel containing GNS, CysNO, and immunotherapy agent was stored at 4 °C.

Analysis

The surface morphology of GNS was analyzed by Fe-SEM transmission electron (field-emission scanning microscopy). The storage modulus and loss modulus of the temperature-sensitive hydrogel were measured using a modular compact rheometer (MCR302, Anton Paar). Thermogravimetric analysis (TGA) was measured in the range of 100 to 800 °C while raising the temperature at a rate of 10 °C/min.

Cumulative Drug Release Experiment

In the cumulative drug release experiment, the temperature-sensitive hydrogel according to the present invention was mixed with fluorescent fluorescein-5-isothiocyanate (FITC) and then dialyzed based on the intensity 0.5 ml of the temperature-sensitive hydrogel according to the present invention was placed in a 12-14 MWCO dialysis membrane, immersed in 5 ml of the dialysate, and the fluorescence (495/525 nm) of the dialysate was measured for 4 days while rotating at 70 rpm at 37 °C. The experiment was repeated three times and expressed as an average.

In Vitro Nitric Oxide Assay

NO (nitric oxide) quantification was performed by Griess assay. Sulfanilic acid is converted into a diazonium salt by nitric oxide. The diazonium salt may be combined with an azo dye and the absorbance at 548 nm may be measured to perform quantitative detection. $1\times10^5$ breast cancer cells (4T1) were seeded in each well of a 24-well plate, treated with the samples and incubated for 4 hours. Then, the cells were washed three times with PBS and irradiated with near-infrared light for 5 min, the cell culture was collected at a predetermined time, and nitric oxide was quantitatively detected using the Griess assay.

Evaluation of Photothermal Effect

In order to evaluate the photothermal effect, GNS and the temperature-sensitive hydrogel according to the present invention were irradiated with near-infrared light (808 nm, 1.5 $W/cm^2$) for 5 min, and imaged with an infrared camera, and the temperature of the sample was then measured for every minute.

To evaluate photothermal effect in in vitro, cells were seeded ($1\times10^4$ cells/well) in 96 well-plate and incubated for 12 h. The cells were treated with GNS and the temperature-sensitive hydrogel according to the present invention at various concentrations (1.5 to 200 μg/mL) and incubated for 4 hours. Then, the well was irradiated with near-infrared light for 5 min and incubated again for 24 hours. Then, cell viability was measured using WST-1 assay.

Cell Live and Dead Assay

Live and dead assay was performed to visually detect whether cells were live or dead. The live cells are stained green (fluorescein diacetate) and dead cells are stained red (propidium iodide). 4T1 cells ($2\times10^4$ cells/well) were seeded on a 24-well plate and incubated in the atmosphere of 5% $CO_2$ at 37 °C for 24 h. Then, GNS was added in each well and PBS was used as a control group. After 4 hours, the cells were treated with an 808 nm laser irradiation at 1.5 $W/cm^2$ for 5 min and further incubated for 24 h. Then, the cells were treated with fluorescein diacetate and propidium iodide. After 5 min, the cells were washed three times with PBS. Whether the cells were dead or live was visualized using a fluorescence microscope.

ROS (Reactive Oxygen Species) Detection Assay

For intracellular ROS detection, 4T1 cells ($2\times10^4$ cells/well) were incubated in 24-well plate with 5% $CO_2$ at 37 °C for 12 h. Cells were treated with various samples treatment with/without lasers and incubated for 4 h. The incubated cells were irradiated with 808 nm NIR laser (1.5 $W/cm^2$) for 5 min and cells were washed with PBS thrice and serum free medium containing DCFH-DA (25 μM) was added into the well plate and incubated for another 20 min. Then, the cells were washed three times with PBS, and the level of fluorescence expression was determined using a fluorescence microscope to confirm the expression level of ROS in the cells.

Western Blot Analysis

The cells seeded in 12 well plates ($5\times10^5$) for 12 h at incubation. The cells were treated samples and incubated for 4 h. Then, cells were irradiated for 5 min (1.5 W/$cm^2$) and further incubated for 6 h. Then, the cells were washed three times with cold PBS, and then were lysed with RIPA containing protease and phosphatase inhibitors. The same amount of cell leachate (20 μg/10 μl) was separated using a 6% SDS-PAGE (sodium dodecyl sulphate-polyacrylamide electrophoresis) gel and then transferred to a PVDF (polyvinylidene-difluoride) membrane. The membrane was blocked with TBS (tris-buffered saline) containing 5% skim milk and 0.1% Tween-20 at room temperature for 1 hour. Then, the cells were visualized using a chemiluminescence detection system treated at 4 °C with primary antibodies (anti-iNOS, anti-IDO) and then secondary antibodies.

In Vivo Photothermal Studies

All animal experiments were performed according to the institutional guidelines of the Institutional Animal Care and Use Committee (IACUC) of Chonnam National University in accordance with National Institutes of Health (NIH) guidelines. Female BALB/C mice (5-6 weeks old) were purchased from Dae Han Bio Link, South Korea, provided with proper food and water, and maintained under pathogen-free conditions. The hair of the animals was shaved, and 4T1 cells ($1\times10^6$ cells/animal) were subcutaneously injected into the animals. Once the tumor reached 100 $mm^3$, the animals were randomly divided into eight groups and intratumorally injected with 50 μL of temperature-sensitive hydrogel according to the present invention. The animals were then exposed to an NIR laser with an excitation wavelength of 808 nm and a power of 2 W/$cm^2$. After 10 min of irradiation, the animals were placed in their cages, and the tumor volumes and body weights were recorded at predetermined time points. After 14 days, the animals were sacrificed, and the resected tumors were photographed and used for further studies.

2. Results

Figure 1A:
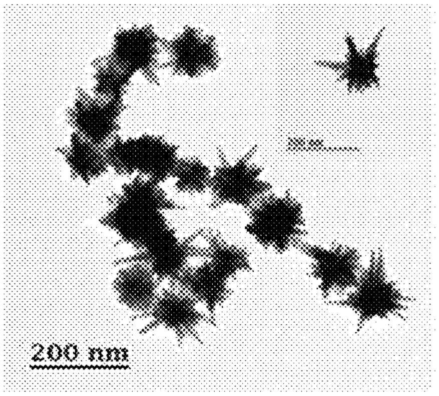
FIG. 1A is a transmission electron micrograph of the gold nanostars (GNS) of the present invention.
Figure 2:
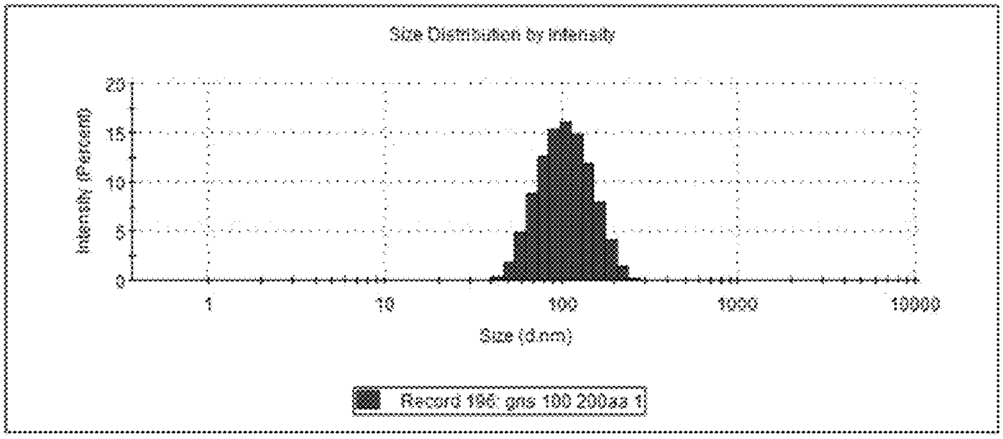
FIG. 2 shows the measured hydrodynamic size of the gold nanostars (GNS) of the present invention.

Preparation of GNS, CysNO; and Preparation of Temperature-Sensitive Hydrogel Containing GNS, CysNO and Immunotherapy Agent of the Present Invention Pluronic F127, which is a temperature-sensitive polymer, has a hydrophobic moiety and thus can hold the drug longer through hydrophobic interaction with hydrophobic drugs. However, Pluronic F127 has the problem of easily disappearing from the body because it forms a weak hydrogel. In the present invention, in order to solve this problem, hyaluronic acid was added thereto to increase viscosity. GNS was added to the hydrogel to obtain photothermal effect, the star-shaped surface thereof was found using an electron microscope (see FIG. 1A), and the size thereof was found to be 110±37.15 nm using an electron microscope and DLS (see FIG. 2).

Figure 1B:
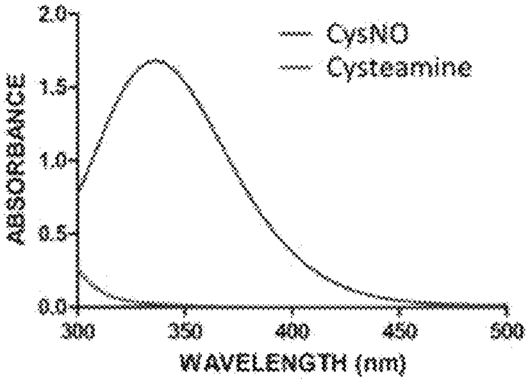
FIG. 1B shows a UV-vis absorbance spectrum of CysNO of the present invention.
Figure 1C:
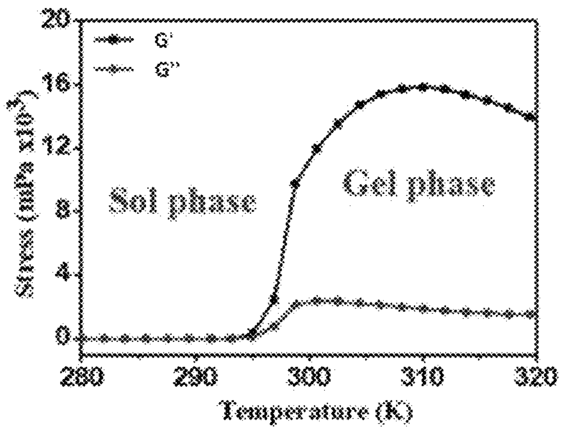
FIGS. 1C and 1D show gelation temperatures of Pluronic F127 and the temperature-sensitive hydrogel according to the present invention measured using a rheometer, respectively (G': storage modulus, G": loss modulus).
Figure 1D:
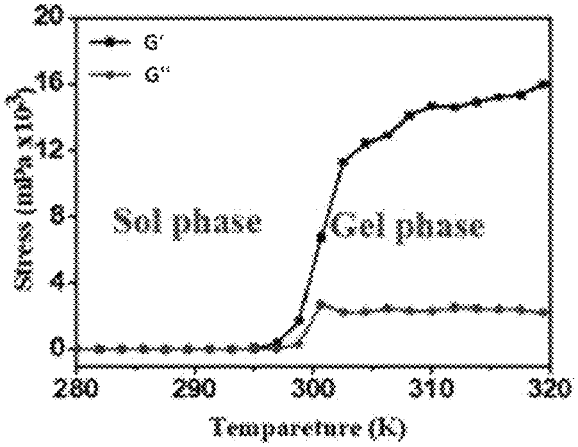
Figure 3:
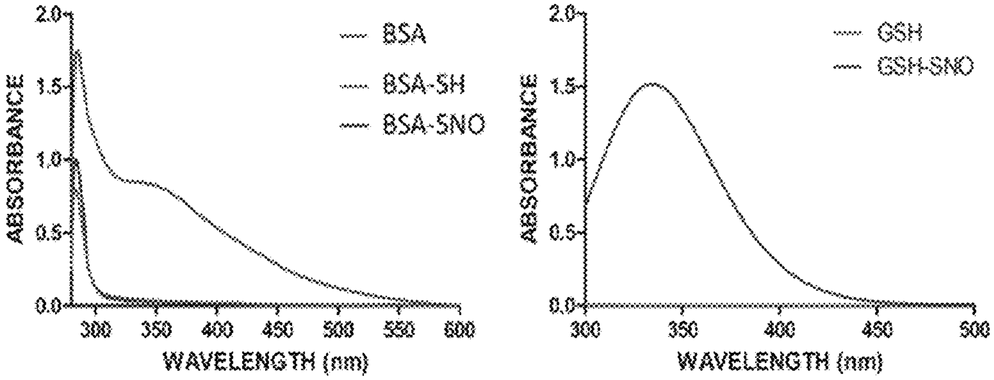
FIG. 3 shows the absorbance spectra of BSA-SNO and GSH-SNO of the present invention.
Figure 4:
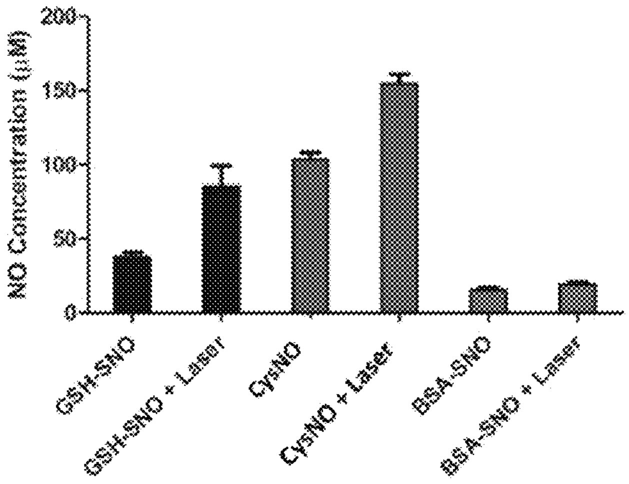
FIG. 4 shows the measured nitric oxide (NO) release concentrations of BSA-SNO, CysNO, and GSH-SNO of the present invention depending on whether near-infrared laser irradiation is performed or not.
Figure 5A:
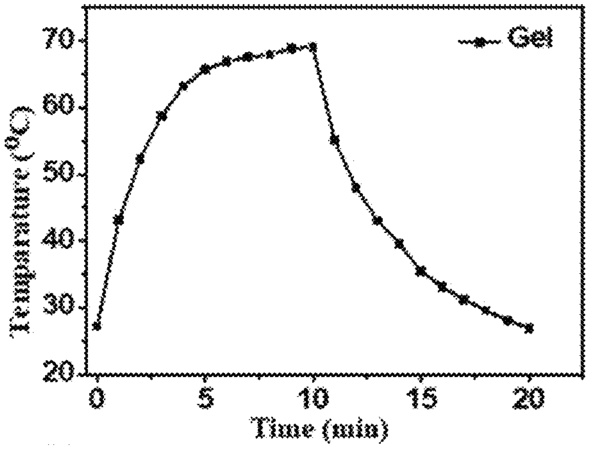
FIGS. 5A and 5C show Thermal plots showing the heating and cooling profiles of the temperature-sensitive hydrogel (5A) and solution (solution state of hydrogel) (5C) of the present invention after irradiation with a near-infrared laser for 10 minutes.
Figure 5B:
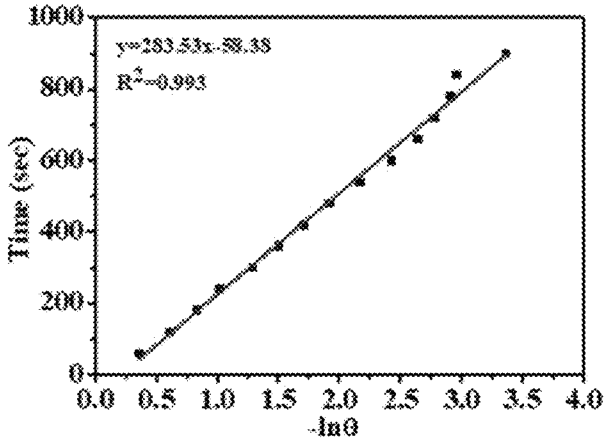
FIGS. 5B and 5D are plots showing linear time versus negative natural logarithimic of friving force temperatures in the temperature-responsive hydrogel (5B) and solution state of hydrogel (5D) according to the present invention in order to determine the time constant of the sample. The slope of the equation represents the time constant of the sample.
Figure 5C:
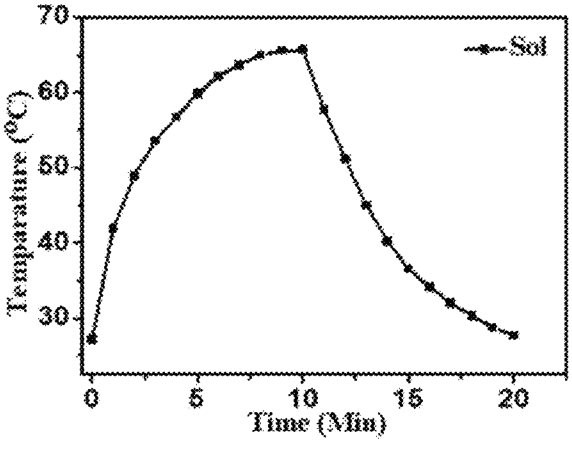
Figure 5D:
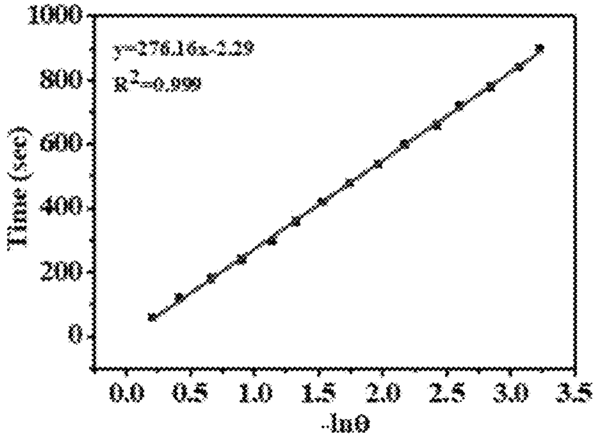

Additionally, we introduced CysNO as a source of NO generation. Initially, we used biological components such as bovine serum albumin (BSA) and glutathione (GSH) to as a source of NO. We confirmed the formation of S-NO by UV-Vis absorbance spectrometry. The peak at 340 nm indicated the S-NO group absorption bands in BSA-SNO, GSH-SNO (see FIG. 3). Thereamong, CysNO showed the highest absorbance and was thus selected as the best candidate for NO release (see FIG. 1B). The results of quantitative measurements of NO as well as absorbance showed that the release of NO was the highest when CysNO was irradiated with near-infrared light (see FIG. 4). The rheological properties of the temperature-sensitive hydrogel according to the present invention were measured using a rheometer. The sol-gel conversion temperature was 299K and the elastic modulus as a function of temperature changed from 295K to 299K when the therapeutic agent and hyaluronic acid were added to Pluronic F127 (see FIGS. 1C and 1D).

Figure 1E:
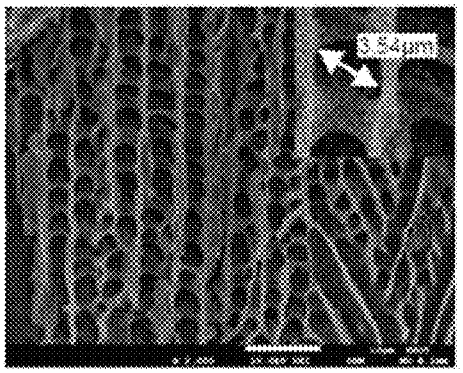
FIG. 1E is a scanning electron micrograph of the temperature-sensitive hydrogel according to the present invention.

In order to determine thermal stability, thermal stability was measured using TGA. It was found that, when irradiated with a near-infrared laser, thermal stability increased (weight loss occurred at higher temperatures) (see FIG. 5). After laser irradiation, the morphology of the temperature-sensitive hydrogel according to the present invention was observed using an electron microscope (see FIG. 1E).

Figure 1F:
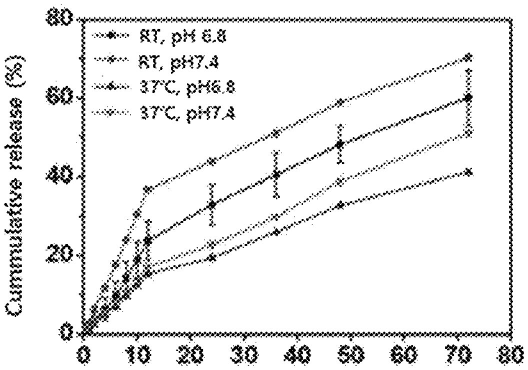
FIG. 1F shows the cumulative drug release behaviors of the temperature-sensitive hydrogel according to the present invention under different temperature and pH conditions.

The temperature-sensitive hydrogel of the present invention has a well-ordered and uniform pore size, which is the optimal condition for sustained drug release. The drug release behavior of the hydrogel of the present invention was observed at a pH of 6.8 and a pH of 7.4 using a model drug (FITC) (see FIG. 1F). Drug release at room temperature was faster than that at 37 °C due to lower viscosity. In addition, drug release was slower at 37 °C and at a low pH due to protonation of the hydrogel, indicating that the drug has suitable physical properties for continuous release of drugs around cancers with low pH.

Figure 6A:
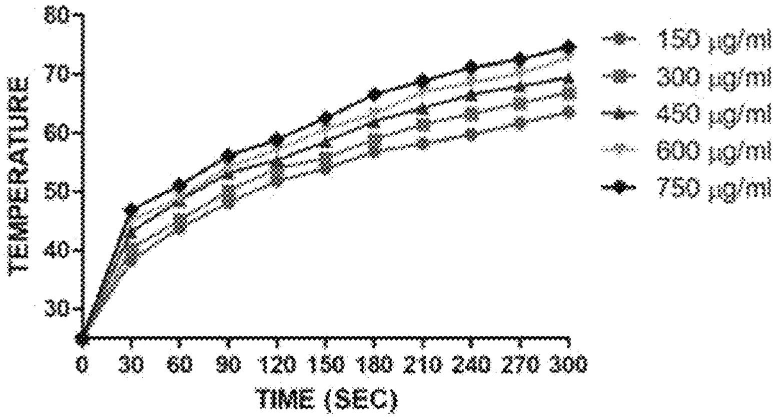
FIGS. 6A and 6B show the photothermal effect and digital photograph of thermal images of gold nanostars (GNS) at different concentrations under irradiation with a near-infrared laser (808 nm, 1.5 W/$cm^2$).
Figure 6B:
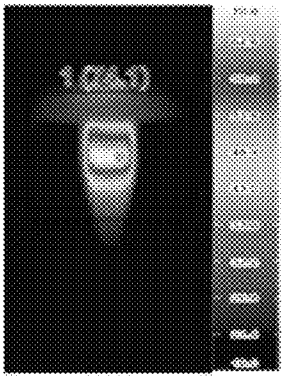
Figure 6C:
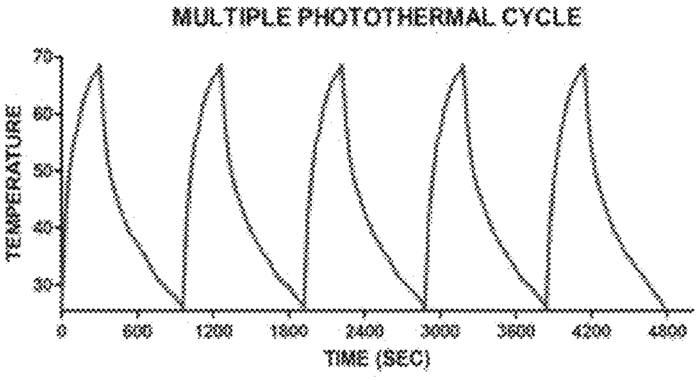
FIG. 6C is a graph showing the photothermal effect when irradiation of gold nanostars (GNS) with the near-infrared laser repeats stopping and starting.
Figure 6D:
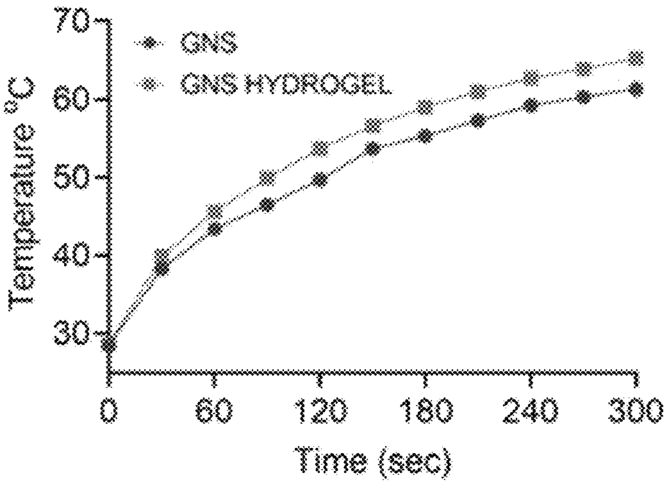
FIGS. 6D and 6E show the photothermal effect and digital photograph of thermal images of gold nanostars (GNS) (100 μg/ml) and hydrogel containing GNS under irradiation with a near-infrared laser (808 nm, 1.5 W/$cm^2$).
Figure 6E:
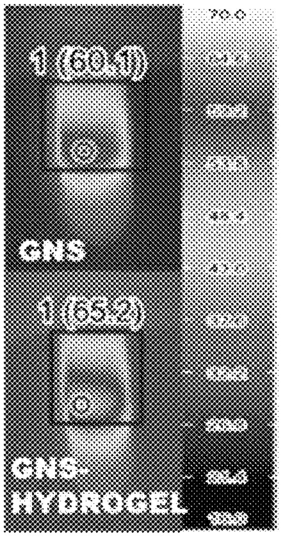
Figure 6F:
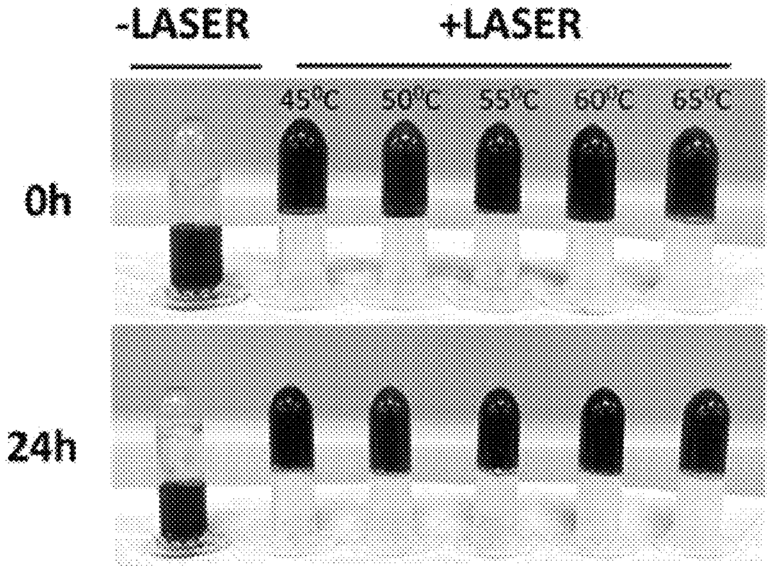
FIG. 6F is an image showing a hydrogel containing gold nanostars (GNS) that is heated by irradiation with a near-infrared laser and stored at room temperature for 24 hours.
Figure 6G:
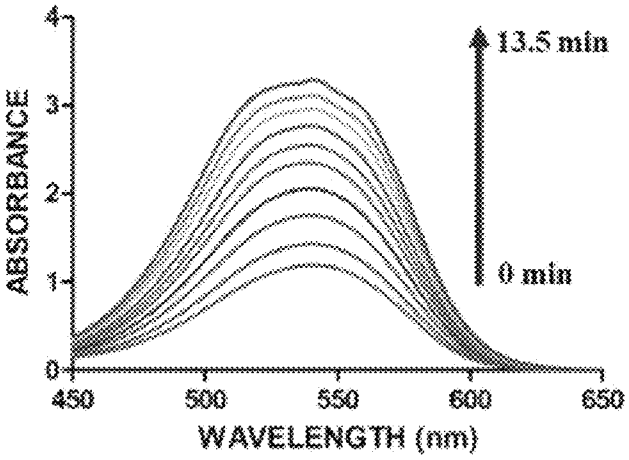
FIG. 6G shows the UV-vis absorption spectra of CysNO with different time point due to nitric oxide (NO) release under Laser irradiation (808 nm).
Figure 6H:
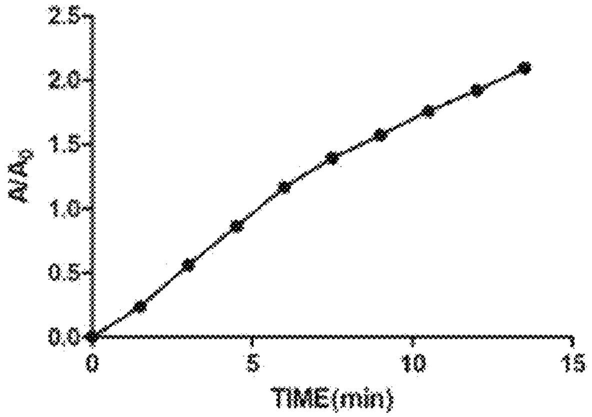
FIG. 6H shows the standard curve of absorbance.
Figure 6I:
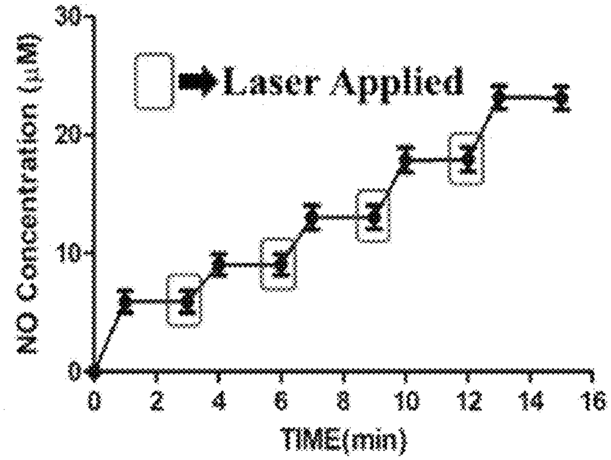
FIG. 6I shows the measured concentration of nitric oxide released from CysNO under laser irradiation every 2 min.

Confirmation of Photothermal Effect and Nitric Oxide Release Under Near-Infrared Irradiation To evaluate photothermal effect of GNS, under NIR laser irradiation, various concentration of GNS were treated with NIR laser and recorded temperature increment. GNS showed significant photothermal conversion efficacy with increased the concentration of GNS and no degradation with retreatment which signifies GNS is a potential candidate for photothermal therapy (see FIGS. 6A to 6C). Then, the temperature-sensitive hydrogel according to the present invention was irradiated with near-infrared light and whether or not the photothermal effect was reduced was determined. The result showed significant arisement in temperature. Interestingly, there is no gel degradation after irradiation up to 24 h (see FIGS. 6D to 6F). The efficiency of the photothermal effect of the temperature-sensitive hydrogel according to the present invention was 61.5%. To investigate the kinetic profile of NO release under laser irradiation, we performed Griess assay at different t time point. The UV-vis absorption spectra confirmed the sustainability of NO release of CysNO under laser irradiation (808 nm, 1.5 W/$cm^2$) (see FIGS. 6G and 6H) and NO release with/without laser was applied which mean NO release will continue only after Laser irradiation (see FIG. 6I).

In Vitro Cytotoxicity Assessment

Figure 7:
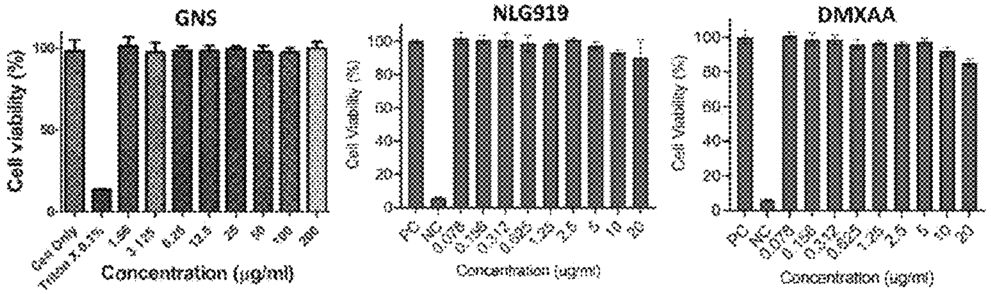
FIG. 7 shows cell viability of 4T1 cells treated by GNS, NLG919 and DMXAA with different concentrations.
Figure 8A:
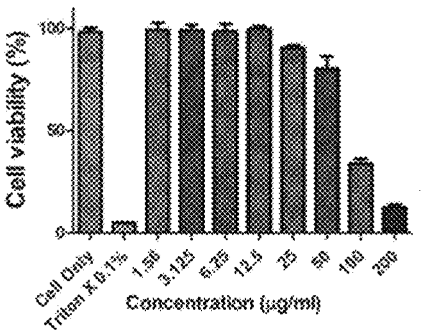
FIGS. 8A and 8B are graphs showing cell viability of 4T1 cells treated by gold nanostars (GNS) (8A) and the temperature-sensitive hydrogel according to the present invention (8B) with different concentrations under laser irradiation (808 nm, 1.5 W/$cm^2$, 5 min), respectively.
Figure 8B:
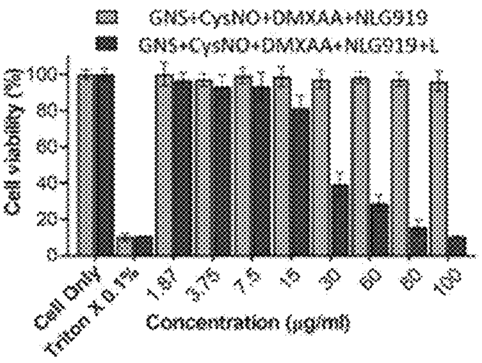
Figure 8C:
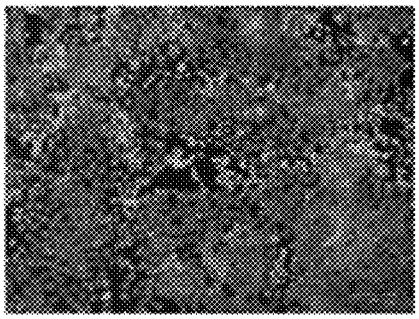
FIGS. 8C to 8F show the results of live and dead assay of each 4T1 cell treatment group under near-infrared laser irradiation (808 nm, 1.5 W/$cm^2$, 5 min) (8C: PBS, 8D: PBS+laser; 8E: GNS, 8F: GNS+laser).
Figure 8D:
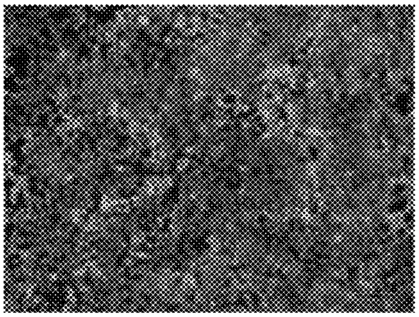
Figure 8E:
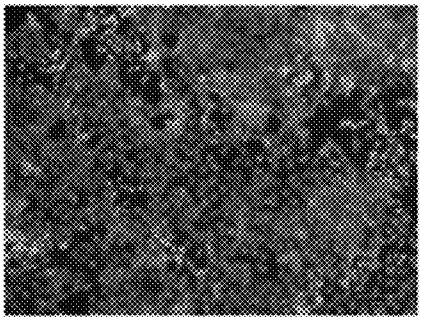
Figure 8F:
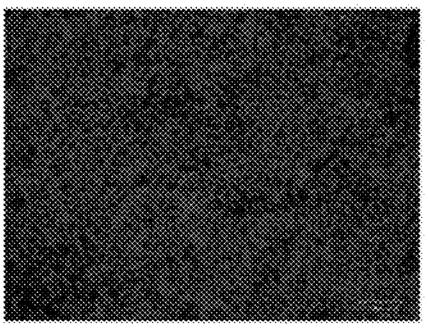

Before investigating the photothermal effect of GNS and the temperature-responsive hydrogel of the present invention, 4T1 cells were treated with different concentrations of GNS, NLG919, and DMXAA for 24 hours. The result of WST-1 analysis showed that GNS, NLG919, and DMXAA exhibited no remarkable biological toxicity to cells even at high concentrations (see FIG. 7). Then, different concentrations of GNS and the temperature-sensitive hydrogel according to the present invention were applied to cells and the photothermal effects of GNS and the temperature-sensitive hydrogel under NIR laser irradiation (808 nm, 1.5 W/$cm^2$, 5 min) were studied. The result showed that, when 100 μg/ml of GNS was irradiated with a laser, the cell viability was 40% (see FIG. 8A), whereas 80 and 100 μg/ml of the temperature-sensitive hydrogel according to the present invention was irradiated with a laser, the cell viability was less than 20% (see FIG. 8B). GNS and the temperature-sensitive hydrogel according to the present invention exhibited cytotoxicity only when irradiated with a near-infrared laser (see FIGS. 8A and 8B). In order to further evaluate cell viability after laser irradiation and sample treatment, live and dead assays were performed. Almost 100% of the cells appeared to survive when treated with PBS, PBS+laser, and GNS, whereas no cells survived when irradiated with GNS+laser (see FIGS. 8C to 8F). The results showed that GNS could initiate cytotoxic properties only under near-infrared laser irradiation.

TABLE 1

Cell viability (%) of various concentrations of GNS upon near-infrared irradiation

| Cell | Triton X | GNS concentration (μg/ml) | | | | | | | |
|---|---|---|---|---|---|---|---|---|---|
| Only | 0.1% | 1.56 | 3.125 | 6.25 | 12.5 | 25 | 50 | 100 | 200 |
| 98.10 ± 3.61 | 5.02 ± 0.28 | 99.30 ± 5.94 | 99.15 ± 4.36 | 98.46 ± 6.13 | 99.72 ± 2.09 | 90.42 ± 2.32 | 80.25 ± 10.36 | 33.90 ± 3.77 | 12.32 ± 2.80 |

TABLE 2

Cell viability (%) of various concentrations of hydrogel of the present invention upon near-infrared irradiation

| NIR | Cell Only | Triton X 0.1% | Hydrogel concentration (μg/ml) 1.87 | 3.75 | 7.5 | 15 | 30 | 60 | 80 | 100 |
|---|---|---|---|---|---|---|---|---|---|---|
| ○ | 100 ± 3.30 | 10.58 ± 0.06 | 96.59 ± 4.20 | 93.31 ± 6.00 | 93.35 ± 7.60 | 81.17 ± 7.10 | 39.41 ± 6.30 | 28.77 ± 4.70 | 15.71 ± 4.10 | 10.19 ± 0.70 |
| X | 99.98 ± 2.40 | 10.23 ± 1.90 | 100.01 ± 6.30 | 96.94 ± 3.30 | 99.16 ± 4.60 | 98.60 ± 5.50 | 97.20 ± 5.00 | 98.32 ± 3.20 | 97.23 ± 3.80 | 96.10 ± 5.50 |

In Vitro ROS Generation and NO Release

Figure 9A:
FIGS. 9A to 9F show the results of DCFDA assay for reactive oxygen species (ROS) measurement of 4T1 cells treated by PBS (9A), GNS (9B), GNS+CysNO (9C), GNS+laser (9D), CysNO+laser (9E) and GNS+CysNO+Laser (9F) under laser irradiation (808 nm, 1.5 W/$cm^2$, 5 min).
Figure 9B:
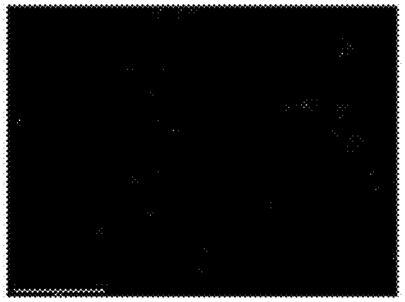
Figure 9C:
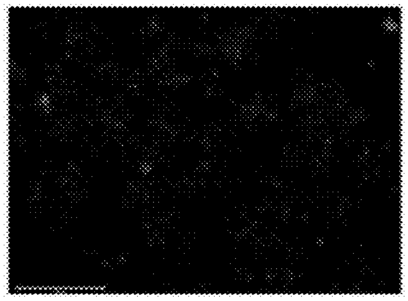
Figure 9D:
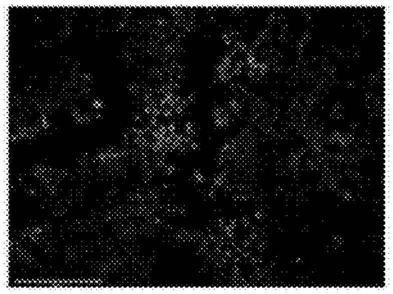
Figure 9E:
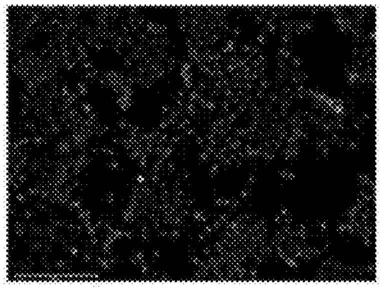
Figure 9F:
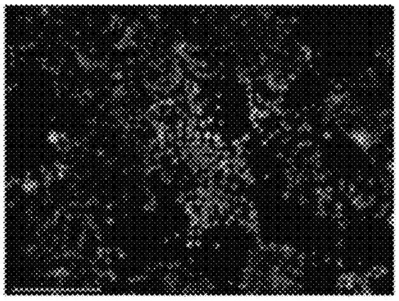
Figure 9G:
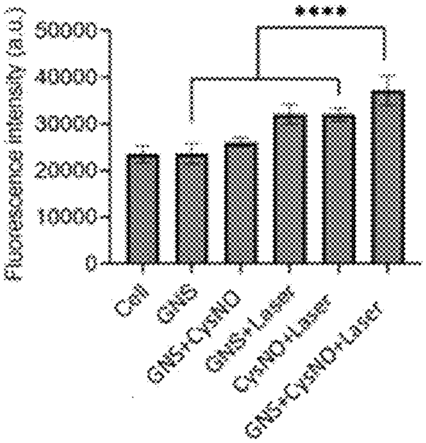
FIG. 9G is a graph showing quantitatively measured fluorescence intensity of generated reactive oxygen species (N=3).
Figure 9H:
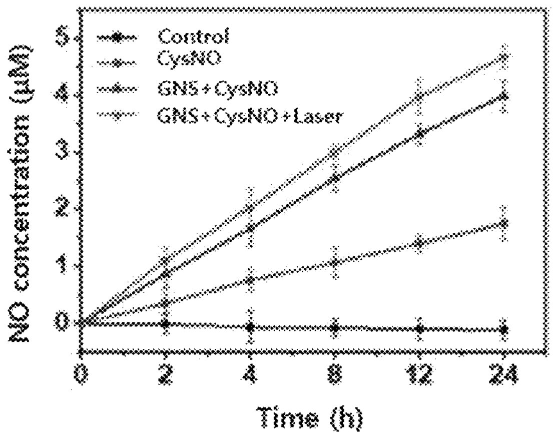
FIG. 9H shows the measured concentration of nitric oxide (NO) released over time from each 4T1 cell treatment group. FIG.
Figure 9I:
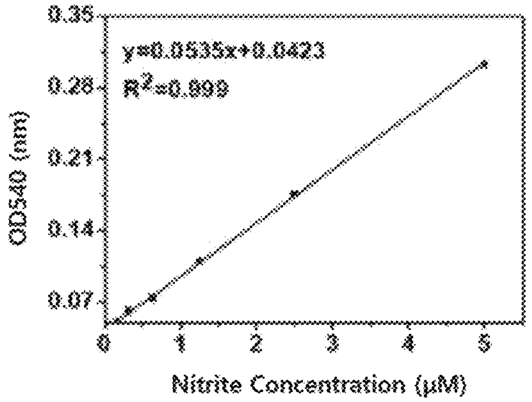

The intracellular ROS production was investigated by fluorescence microscopy with cell permeable green fluorescence ROS indicator DCFDA (2',7'-dichlorofluorescin diacetate). The result showed that cells were treated with control (PBS), GNS and GNS+CysNO no significant generation of ROS (see FIGS. 9A to 9C), whereas the cells were treated with GNS, CysNO and GNS+CysNO and then irradiated with laser showed significant ROS production (see FIGS. 9D to 9F). The results show that laser irradiation induces generation of significant amounts of ROS. The cell media was collected at predetermined time points. Griess assay was performed to quantify NO release from the cells. The result showed that GNS+CysNO exhibited higher NO generation upon laser irradiation (808 nm) compared to the control (PBS), CysNO, and GNS+CysNO, indicating that NO increased upon laser irradiation (see FIGS. 9H to 9I). The increment of NO release could be attributed under laser treatment.

ANTI-Tumor Effect of Temperature-Sensitive Hydrogel of Present Invention in 4T1 Tumor Mice Under Laser Irradiation Mice with 4T1 tumors were treated with various samples with or without near-infrared laser irradiation after the tumor size reached 100 $mm^3$. The tumor volume of the mice with 4T1 tumors that underwent laser irradiation was significantly reduced compared to the control (PBS) and GNS+CysNO+NLG919 (hydrogel) treatments. Interestingly, treatment with GNS+CysNO+NLG919 (hydrogel)+laser and GNS+CysNO+NLG919+DMXAA (hydrogel) had superior tumor delay effect (The tumor volume did not increase) compared to GNS+laser and GNS+CysNO (hydrogel)+laser (see FIGS. 11 and 13 and Table 3). The results showed that, even if the tumor is removed, the tumor grows again after a predetermined period of time in the absence of an immune-activating drug. Therefore, it was determined that immunotherapy in addition to photothermal therapy was necessary to completely remove the tumor. Here, NLG919 and DMXAA played an important role in completely removing the tumor. Meanwhile, there was no significant difference in body weight between treated and untreated mice, which indicates that photothermal therapy and immunotherapy were not toxic (see FIG. 12).

TABLE 3

Tumor volume ($mm^3$) over time of each treatment group of 4T1 tumor mice

| Treatment | Period (day) | | | | | | | |
|---|---|---|---|---|---|---|---|---|
| | 0 | 2 | 4 | 6 | 8 | 10 | 12 | 14 |
| PBS | 767.5 | 1100 | 1404.2 | 1679.2 | 1888.8 | 1996.8 | 2187 | 2260 |
| GNS + laser | 423.1 | 211.8 | 118.5 | 180.9 | 443.1 | 831.1 | 1104.6 | 1376 |
| GNS + CysNO (hydrogel) + laser | 581.9 | 143.4 | 157.9 | 194.8 | 419.9 | 886.8 | 9778.9 | 1130.9 |
| GNS + CysNO + NLG919 (hydrogel) | 574.6 | 665.3 | 1009.1 | 1013.3 | 1239.6 | 1375.2 | 1410.8 | 1442.4 |
| GNS + CysNO + NLG919 (hydrogel) + laser | 496.3 | 210.3 | 146.1 | 135.4 | 122.1 | 131.7 | 151.3 | 152.5 |
| GNS + CysNO + NLG919 + DMXAA (hydrogel) + laser | 434.9 | 195.2 | 87.6 | 58.2 | 37.2 | 43.4 | 48.2 | 59.2 |

Hereinbefore, the present invention has been described with reference to preferred embodiments. Those skilled in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description and all differences equivalent thereto should be construed as falling into the scope of the present invention.

EXPLANATION OF REFERENCE NUMERALS

BSA: Bovine serum albumin
GSH: Glutathione
Cys: Cysteine
NO: Nitric Oxide
GNS: Gold Nanostars
Fe-SEM: Field-Emission scanning electron microscopy
TGA: Thermogravimetric Analysis
FITC: Fluorescein-5-isothiocyanate
TBS: Tris-buffered saline
iNOS: Inducible nitric oxide synthase
IDO: Indoleamine 2,3-dioxygenase

The invention claimed is:

1. A temperature-sensitive hydrogel for treating cancer, as active ingredients, comprising:
gold nanostars;
S-nitrosocysteine; and
an immunotherapeutic agent.

2. The temperature-sensitive hydrogel according to claim 1, wherein the gold nanostars generate heat when irradiated with light.

3. The temperature-sensitive hydrogel according to claim 1, wherein the immunotherapeutic agent is a stimulator of interferon genes, an indoleamine 2,3-dioxygenase (IDO) inhibitor, or a combination thereof.

4. The temperature-sensitive hydrogel according to claim 1, further comprising a gelling polymer.

5. The temperature-sensitive hydrogel according to claim 4, wherein the gelling polymer comprises at least one selected from the group consisting of hyaluronic acid, Poloxamer 407, purified agar, agarose, gellan gum, alginic acid, carrageenan, cassia gum, xanthan gum, galactomannan, glucomannan, pectin, cellulose, guar gum and locust bean gum.

6. The temperature-sensitive hydrogel according to claim 1, wherein the hydrogel generates heat and releases nitric oxide (NO) when irradiated with near-infrared light.

7. A photothermal composition for treating cancer comprising the temperature-sensitive hydrogel according to claim 1 as an active ingredient.

8. The photothermal composition according to claim 7, wherein the cancer is selected from the group consisting of brain tumor, benign astrocytoma, malignant astrocytoma, pituitary adenoma, meningioma, cerebral lymphoma, oligodendroglioma, intracranial tumor, ependymoma, brainstem tumor, head and neck tumor, laryngeal cancer, oropharyngeal cancer, nasal cancer, nasopharyngeal cancer, salivary gland cancer, hypopharyngeal cancer, thyroid cancer, oral cancer, thoracic tumor, small cell lung cancer, non-small cell lung cancer, thymic cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colon cancer, anal cancer, bladder cancer, kidney cancer, male genital tract tumor, penile cancer, prostate cancer, female genital tract tumor, cervical cancer, endometrial cancer, ovarian cancer, uterine sarcoma, vaginal cancer, female external genital cancer, female urethral cancer, and skin cancer.

9. The photothermal composition according to claim 7, wherein the composition is a composition for subcutaneous injection, intramuscular injection, intraperitoneal injection, transdermal injection, or intralesional injection.

10. A method of preparing a photothermal composition for treating cancer, the method comprising:
a) synthesizing S-nitrosocysteine;
b) synthesizing gold nanostars;
c) mixing a gelling polymer, S-nitrosocysteine, gold nanostars, and water; and
d) adding an immunotherapeutic agent to a mixture obtained in step c), followed by stirring.

11. The method according to claim 10, wherein the gelling polymer comprises at least one selected from the group consisting of hyaluronic acid, Poloxamer 407, purified agar, agarose, gellan gum, alginic acid, carrageenan, cassia gum, xanthan gum, galactomannan, glucomannan, pectin, cellulose, guar gum, and locust bean gum.

12. The method according to claim 10, wherein the immunotherapeutic agent is a stimulator of interferon genes, an indoleamine 2,3-dioxygenase (IDO) inhibitor, or a combination thereof.

* * * * *